United States Patent
Huttner et al.

[11] Patent Number: 5,972,021
[45] Date of Patent: Oct. 26, 1999

[54] TISSUE APPROXIMATION FORCEPS AND METHOD

[75] Inventors: James J. Huttner; David I. Kinsel, both of Sylvania, Ohio

[73] Assignee: Bionix Development Corporation, Toledo, Ohio

[21] Appl. No.: 09/060,093

[22] Filed: Apr. 14, 1998

Related U.S. Application Data

[63] Continuation-in-part of application No. 08/967,971, Nov. 12, 1997.

[51] Int. Cl.$^6$ ........................................... A61B 17/50
[52] U.S. Cl. ..................... 606/210; 606/205; 294/99.2
[58] Field of Search ................... 606/205, 210, 606/211, 207; D28/55; D24/143; 294/99.2, 3; D7/686

[56] References Cited

U.S. PATENT DOCUMENTS

| | | | |
|---|---|---|---|
| 3,611,842 | 10/1971 | Skipper . | |
| 4,212,305 | 7/1980 | Lahay | 606/210 |
| 4,452,106 | 6/1984 | Tartaglia | 294/99.2 |
| 5,019,091 | 5/1991 | Porat et al. | 606/205 |
| 5,156,431 | 10/1992 | Lowe | 606/210 |
| 5,514,148 | 5/1996 | Smith, III | 606/151 |
| 5,611,794 | 3/1997 | Sauer et al. | 606/8 |
| 5,622,492 | 4/1997 | Eli . | |
| 5,752,973 | 5/1998 | Kieturakis | 606/207 |

OTHER PUBLICATIONS

The International Search Report for PCT/US98/23958 which is based on U.S. Serial No. 08/967,971. U.S. S/N 08/967,971 is claimed as priority for the above–identified application.

A package insert from Dermabond Topical Skin Adhesive, Manufactured for Ethicon, Inc. by Closure Medical Corp.

Evaluation and Management of Traumatic Lacerations, by Adam J. Singer, M.D. et al., as reprinted from *The New England Journal of Medicine*, vol. 337, Oct. 16, 1997 pp. 1142–1147.

*Primary Examiner*—Michael Buiz
*Assistant Examiner*—Tan-Uyen T. Ho
*Attorney, Agent, or Firm*—Emch, Schaffer, Schaub & Porcello Co., L.P.A.

[57] ABSTRACT

The present invention is a method of approximating a wound or laceration without everting the wound edges and tissue approximation forceps to practice the method. The tissue approximation forceps include handle members which mount grip members having grip surfaces. The grip surfaces are moved toward the skin where the grip surfaces engage the skin while remaining generally parallel to the skin surface. The grip surfaces frictionally hold the engaged skin surfaces while the handle members are moved from an uncompressed position to a compressed position. The grip members can be moved toward or away from one another to approximate the edges of the wound or laceration without everting the wound edges. Tissue adhesive is then applied.

17 Claims, 6 Drawing Sheets

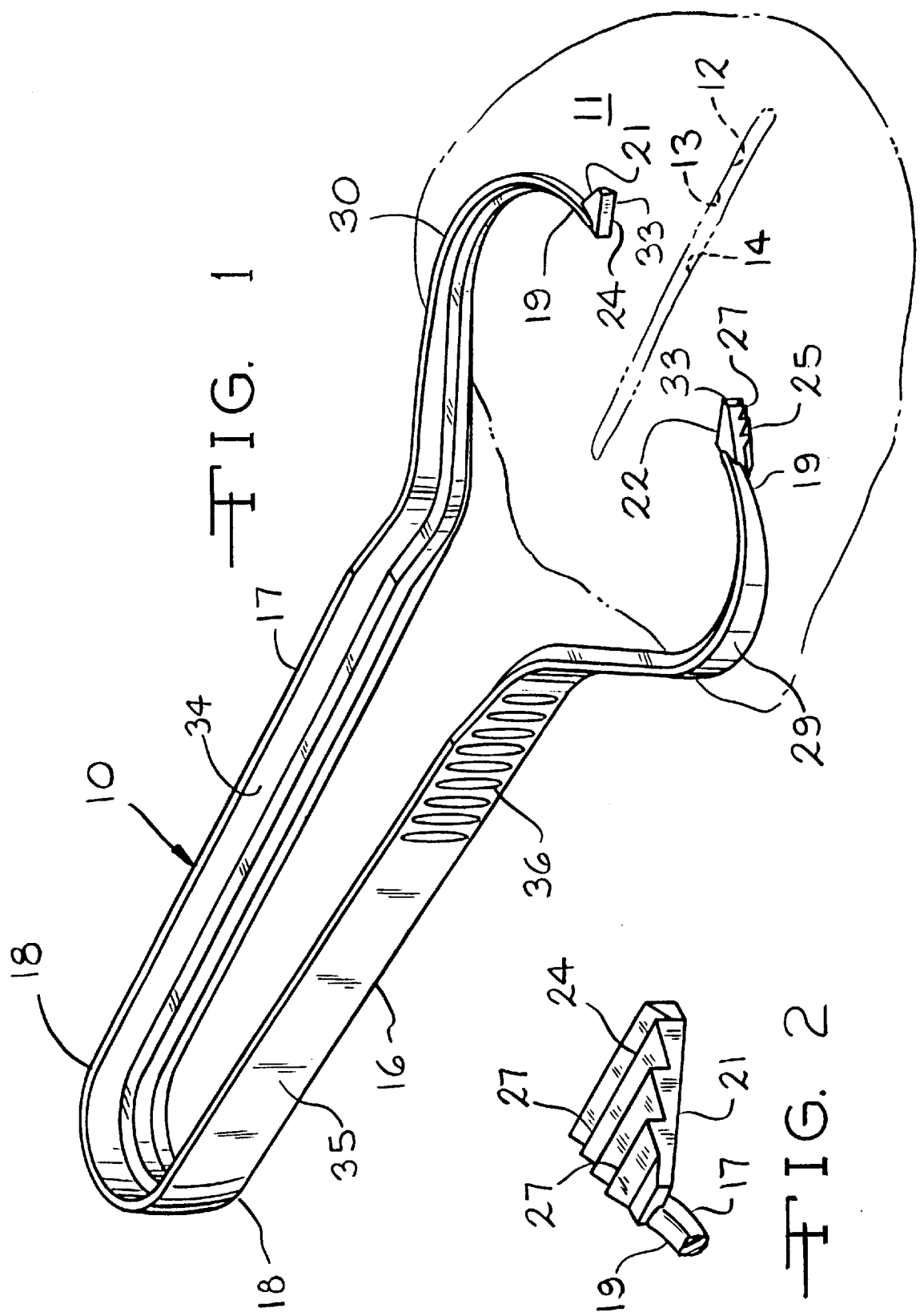

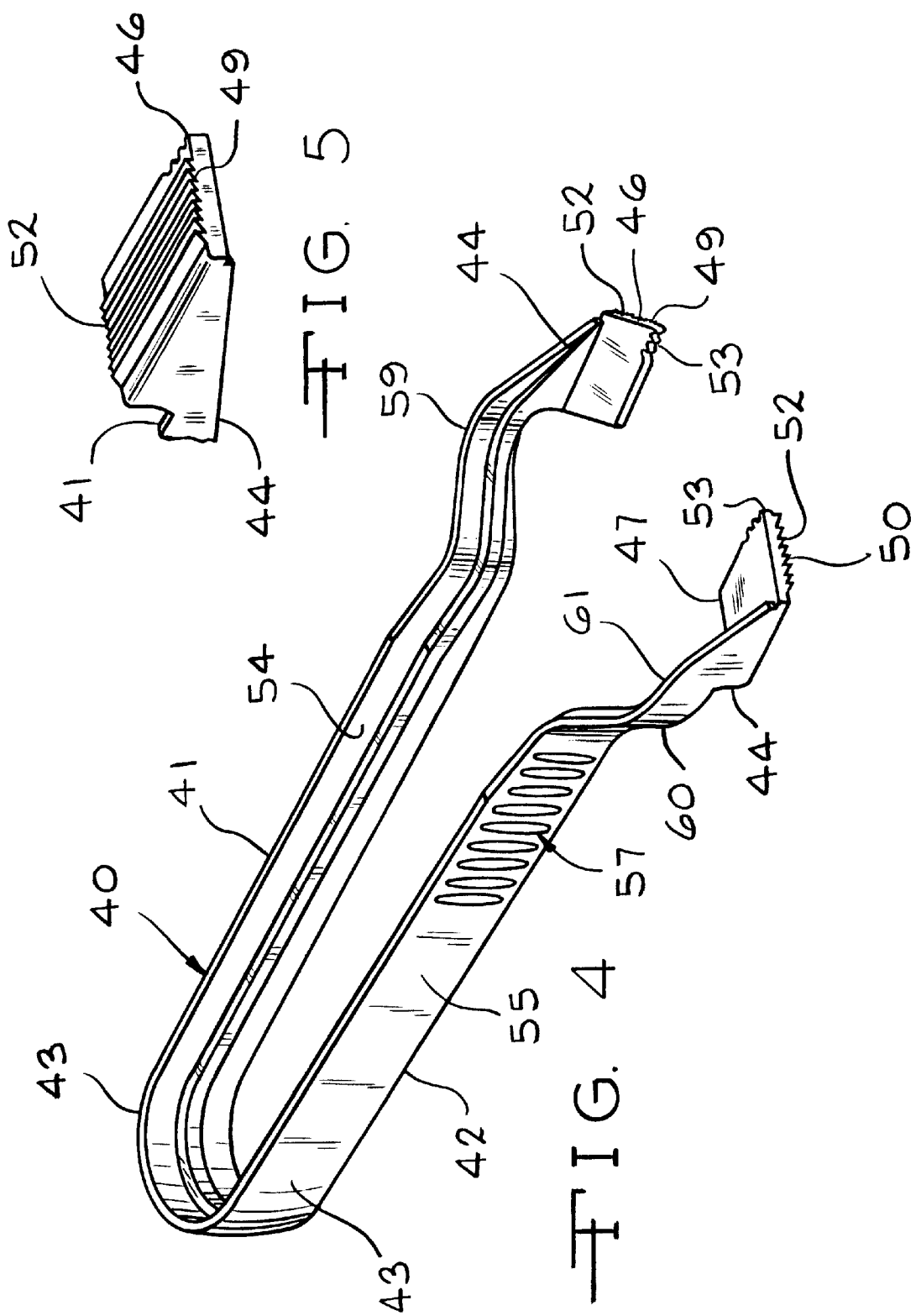

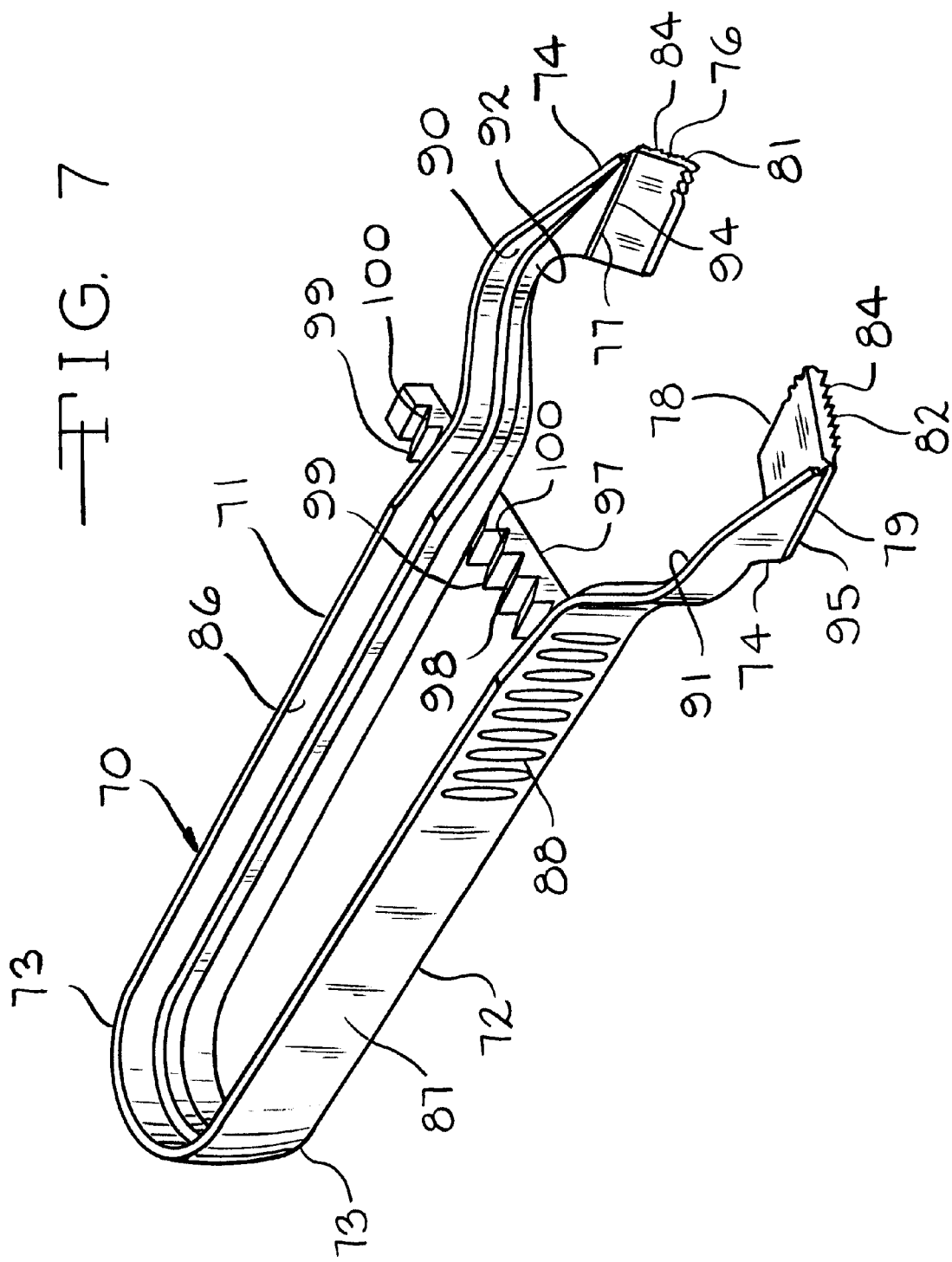

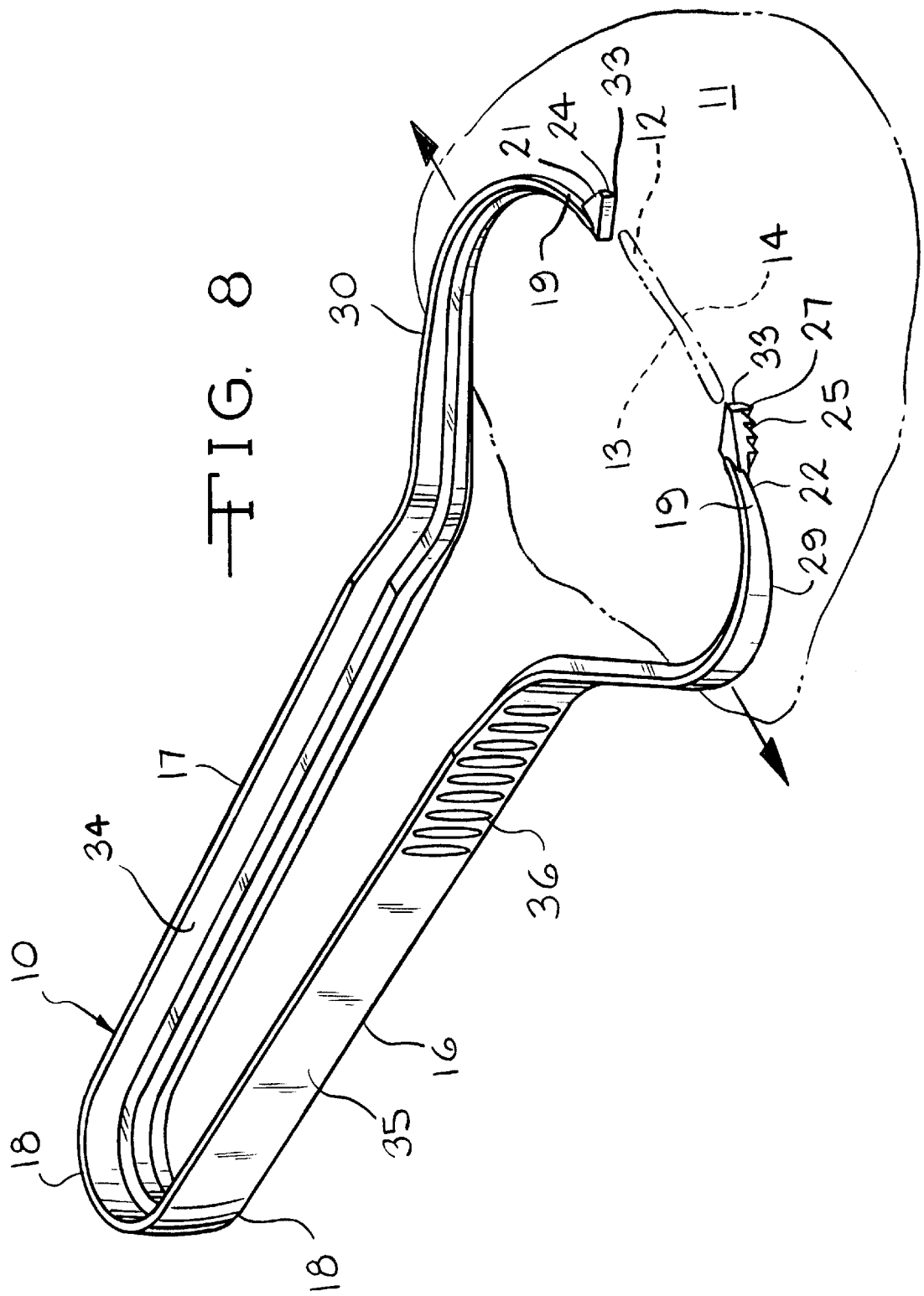

TISSUE APPROXIMATION FORCEPS AND METHOD

RELATED APPLICATION

The present application is a continuation-in-part of application Ser. No. 08/967,971 filed Nov. 12, 1997.

BACKGROUND OF THE INVENTION

The present invention is directed to tissue approximation forceps and method. The tissue approximation forceps of the present invention close a wound without everting the wound edges. The forceps are particularly useful when approximating a wound where tissue adhesive is to be used to secure the approximated wound edges.

Tissue adhesives using cyanoacrylate esters are used for the closure of simple wounds and lacerations. These tissue adhesives are quick and easy to apply. They polymerize readily upon contact with body fluids and tissues and are relatively non-toxic. Of the available cyanoacrylates, butyl esters and octyl esters are preferred for use in medical applications. The butyl and acetyl monomers polymerize into an adhesive that is tougher and more flexible than, for example, methyl ester versions. This yields a stronger wound repair. It has also been found that the longer chain monomers are less tissue toxic than methyl esters.

The proper use of cyanoacrylate tissue adhesives also affects their toxicity. Because the adhesives are absorbable, exposing a raw tissue surface to the adhesive enhances the toxic effects. When using tissue adhesives, it is recommended that the wound edges not be everted. Eversion can, for example, produce a V-shaped channel that retains a quantity of tissue adhesives and also exposes more of the cut edge of the adjacent tissue to the potentially toxic adhesive.

Prior art tissue forceps have many types of mating gripping surfaces, including rat-tooth surfaces, serrated surfaces and crossed hatched surfaces. The gripping surfaces of many prior tissue forceps close in a direction perpendicular to the surface of the skin. Normally, the prior art forceps indent the skin and evert the wound edges during closure.

Other types of prior art forceps or closing devices include clamps for approximating tissue sections as shown in U.S. Pat. Nos. 5,514,148 and 5,611,794.

The tissue approximation forceps and method, according to the present invention, approximates the tissue edges adjacent a wound or laceration without everting the wound edges.

SUMMARY OF THE INVENTION

The present invention is directed to an improved tissue approximation method and to improved tissue approximation forceps. The tissue approximation forceps include spaced grip surfaces which are moved toward the skin on opposite sides of the wound or laceration. The grip surfaces are moved in a direction generally parallel to the skin surfaces. The grip surfaces of the tissue approximation forceps engage the skin with the grip surfaces being applied over extended areas of the skin while remaining generally parallel to the skin surface. The grip surfaces of the tissue approximation forceps frictionally hold the engaged skin surfaces. Finally, by compressing the tissue approximation forceps, the grip surfaces are normally moved toward one another to approximate the wound or laceration without everting the skin edges. After approximation, a gap is defined between the grip surfaces for viewing the approximated wound and applying the tissue adhesive.

In a preferred embodiment of the tissue approximation forceps, according to the present invention, the forceps include a pair of handle members which are joined at one end. Grip members are mounted on the second ends of the handle members. Preferably, the handle members have offsets which define a large viewing area when the forceps are closed. The grip members have grip surfaces which are generally parallel to the skin surface. When the handle members are moved together, the grip members and their grip surfaces are moved toward each other to approximate the wound or laceration. The grip members define a gap when in the compressed position.

BRIEF DESCRIPTION OF THE DRAWINGS

FIG. 1 is a perspective view of tissue approximation forceps, according to the present invention, in an uncompressed position;

FIG. 2 is an enlarged fragmentary view of one of the grip members of the tissue approximation forceps shown in FIG. 1;

FIG. 4 is a perspective view of another embodiment of tissue approximation forceps, according to the present invention, in an uncompressed position;

FIG. 5 is an enlarged fragmentary view of one of the grip member of the tissue approximation forceps shown in FIG. 4;

FIG. 7 is a perspective view of a still further embodiment of tissue approximation forceps, according to the present invention; and FIG. 8 is a view, similar to FIG. 1, showing another embodiment of the method of use.

DETAILED DESCRIPTION OF THE PREFERRED EMBODIMENTS

Figure 3:
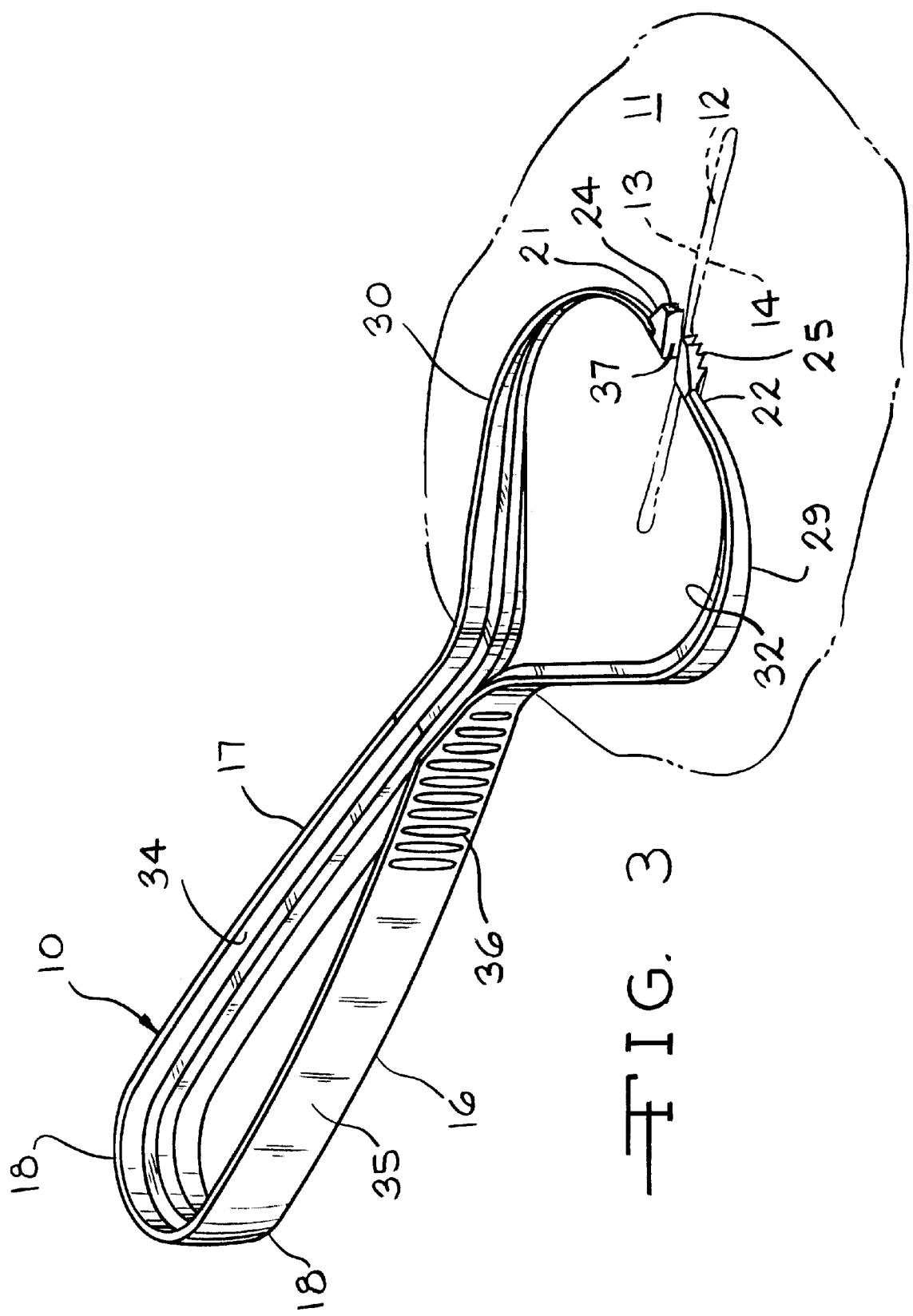
FIG. 3 is a view, similar to FIG. 1, showing the tissue approximation forceps in a compressed position.

Tissue approximation forceps, according to the present invention, are generally indicated in FIG. 1 by the reference number 10. A portion of a patient's skin surface is indicated by the reference number 11. A wound 12 having spaced edges 13 and 14 is also indicated in FIG. 1.

The tissue approximation forceps 10 include a pair of handle members 16 and 17. The handle members 16 and 17 include first ends 18 and second ends 19. The first ends 18 of the handle member 16 and 17 are joined together as shown in FIG. 1.

A first grip member 21 is mounted to the second end 19 of the handle member 17. A second grip member 22 is mounted to the second end 19 of the handle member 16. The grip member 21 defines a grip surface 24 and the grip member 22 defines a grip surface 25. As shown in FIG. 2, the grip surfaces 24 and 25 include a plurality of projections 27 which are disposed substantially perpendicular to the skin surface 11. In the present embodiment, the projections 27 are comprised of a plurality of longitudinally extending parallel projections having generally V-shaped cross-sections.

Referring to FIG. 1, in the present embodiment, the pair of handle members 16 and 17 include offset portions 29 and 30 located adjacent the grip members 22 and 21. The offset portions 29 and 30 are generally bow shaped and define a viewing area, when the second ends 19 of the handle members 16 and 17 are in the compressed position, as shown in FIG. 3. The offset portions 29 and 30 by defining the viewing area provide a better work area to the wound 12 as opposed to prior art forceps which tend to obscure the work area.

Referring to FIG. 3, when the grip members 21 and 22 are moved to the compressed position shown, the grip members 21 and 22 define a gap 37. The gap 37 which is normally between 0.3 cm and 0.6 cm allows the tissue adhesive to be applied and is an important feature.

The grip members 21 and 22 define gripping tips 33 which are used to manipulate tissue on flap lacerations prior to approximation.

Referring to FIG. 1, the opposed handle members 16 and 17 define inner surfaces 34 and outer surfaces 35. In the present embodiment, the outer surface 35 defines a textured pattern 36. The textured pattern 36 provides a better holding surface for the user.

The tissue approximation forceps 10, according to the present invention, may be made of various materials including metal compositions. However, plastic material is preferred. Polyethylene, polybutylene and other non-wettable compositions or materials can be utilized. A preferred plastic material is polybutylene terephthalate.

Referring to FIG. 1, the skin surface 11 of the patient is generally planar. The method of using the tissue approximation forceps 10 includes moving the grip members 21 and 22 and the grip surfaces 24 and 25 toward the skin surface 11, while in an uncompressed position. The grip surfaces 24 and 25 are spaced from one another and positioned on opposite sides of the wound or laceration 12. The grip surfaces 24 and 25 are generally parallel to the skin's surface 11. The grip surfaces 24 and 25 are moved toward the skin and engage the skin surface 11 with the grip surfaces 24 and 25 being positioned over extended areas of the skin while the grip surfaces remain generally parallel to the skin surface 11. The projections 27 engage the skin 11 and the handle members 16 and 17 are moved toward the compressed position, shown in FIG. 3. The grip surfaces 24 and 25 of the grip members 21 and 22 frictionally hold the engaged skin surfaces as the grip member 21 and 22 are moved toward one another to approximate the wound or laceration without everting the skin edges. The grip surfaces 24 and 25 define the gap 37.

Tissue adhesive may then be applied while the user has a satisfactory work area provided by the gap 37 of the tissue approximation forceps 10.

Another method of use of the tissue forceps, according to the present invention is shown in FIG. 8. In this embodiment, the grip members 21 and 22 and the grip surfaces 24 and 25 are moved toward the skin surface 11. The grip surfaces 24 and 25 are spaced from one another and positioned adjacent the ends of the wound 11 along the longitudinal axis. The grip surfaces 24 and 25 are parallel to the skin's surface 11. The handle members 16 and 17 and the grip surfaces 24 and 25 are then moved outwardly away from one another. The outward movement results from the elasticity of the slightly compressed handle members 16 and 17 and, if necessary, by additional manual force. This outward movement approximates the wound 12 while giving the physician a larger viewing and work area.

Figure 6:
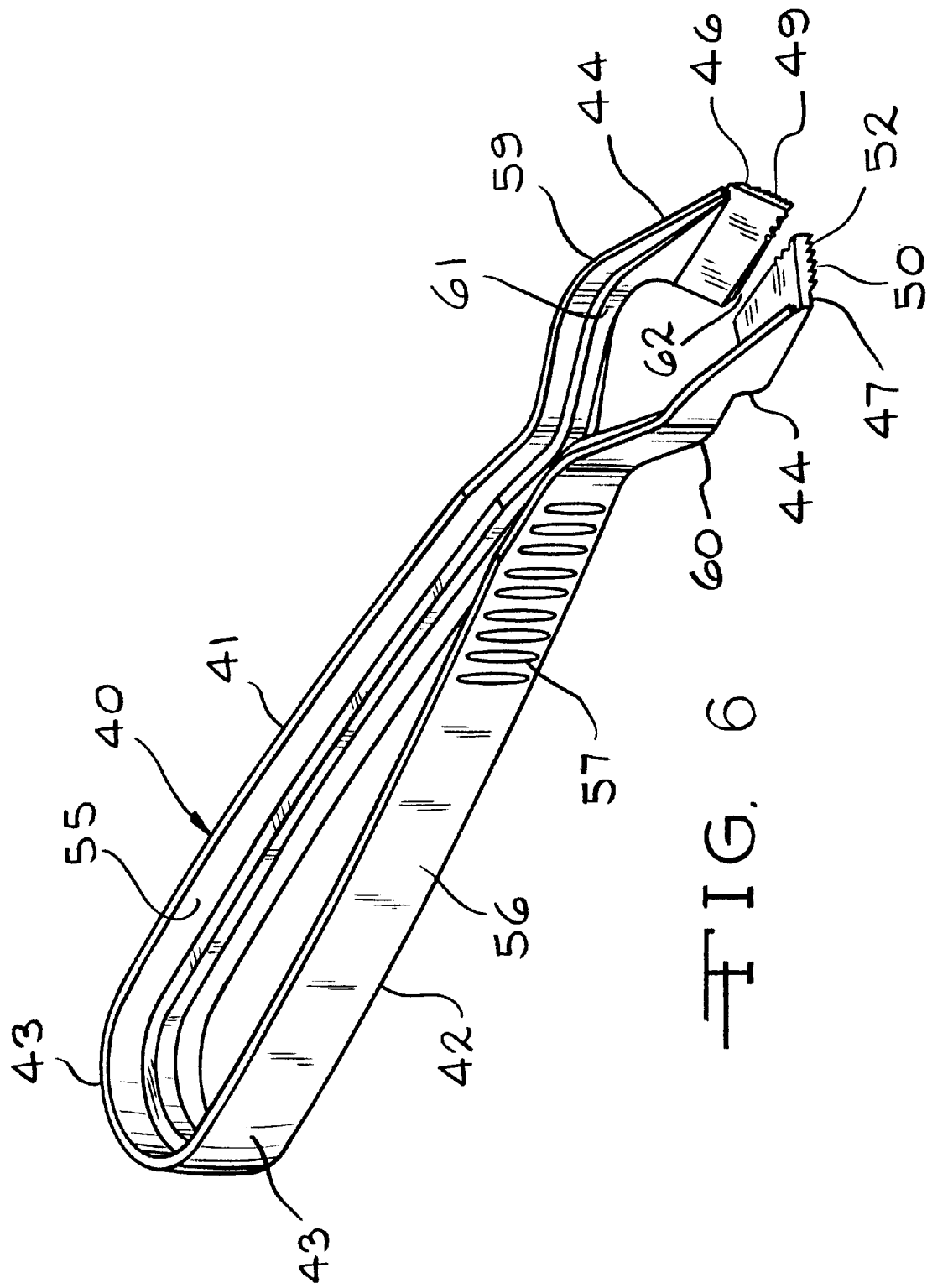
FIG. 6 is a view, similar to FIG. 4, showing the tissue approximation forceps in a compressed position.

Another embodiment of tissue approximation forceps, according to the present invention, is generally indicated by the reference number 40 in FIGS. 4, 5 and 6. The tissue approximation forceps 40 include handle members 41 and 42. The handle members 41 and 42 include first ends 43 which are joined together and second ends 44. A grip member 46 is connected to the handle member 41 adjacent the second end 44. Similarly, a grip member 47 is connected to the handle member 42 adjacent the second end 44. The grip member 46 includes a large generally polygonal grip surface 49 and the grip member 47 includes a similar grip surface 50. A plurality of projections 52 are provided on the grip surfaces 49 and 50. In the present embodiment, the projections 52 are disposed substantially perpendicular to the surface of the skin when the grip members 46 and 47 engage the skin of the patient. In the present embodiment, the projections 52 comprise a plurality of longitudinally extending parallel projections, having generally V-shaped cross-sections. The grip members 46 and 47 define gripping tips 53 which are used to manipulate tissue on flap lacerations prior to approximation. The handle members 41 and 42 of the forceps 40 have inner surfaces 54 and outer surfaces 55. In the present embodiment, the outer surfaces 55 of the handle members 41 and 42 include textured patterns 57 for providing a good holding surface.

Referring to FIGS. 4 and 6, the handle member 41 includes an offset portion 59 adjacent the second end 44. The handle member 42 includes an opposed offset portion 60 adjacent its second end 44. The offset portions 59 and 60 define a viewing area 61 as best seen in FIG. 6. The viewing area 61 provides a better work area when the tissue approximation forceps 40 are moved between the uncompressed position shown in FIG. 4 and the compressed position shown in FIG. 6. When the forceps 40 are moved to the compressed position, the grip members 46 and 47 define a gap 62. The gap 62 is normally between 0.3 cm and 0.6 cm. The gap 62 allows tissue adhesive to be applied while viewing the approximated wound.

The method of using the tissue approximation forceps 40 is generally the same as described with respect to the method of use of the tissue approximation forceps 10.

Still another embodiment of tissue approximation forceps, according to the present invention, is generally indicated by the reference number 70 in FIG. 7. The forceps 70 include handle members 71 and 72 having first ends 73 which are joined together and second ends 74. A grip member 76 is pivotally mounted adjacent the second end 74 of the handle member 71 by a hinge 77. Similarly, a grip member 78 is pivotally mounted to the second end 74 of the handle member 72 by a hinge 79. The hinges 77 and 79 allow the grip members 76 and 78 approximately 30° of rotation with respect to a parallel surface, such as the skin of a patient.

The grip member 76 includes a grip surface 81 and the grip member 78 includes a grip surface 82. The grip surfaces 81 and 82 define a plurality of generally V-shaped parallel projections 84. The plurality of projections 84 extend generally perpendicular to the major surface of the grip members 76 and 78 and are also generally perpendicular to the skin surface of the patient when the grip surfaces 81 and 82 engage the skin. The handle member 71 and 74 have inner surfaces 86 and outer surfaces 87. The outer surfaces 87 of both handle members 71 and 72 define a textured pattern 88 which provides a better holding surface for the hands of a user.

The handle member 71 includes an offset portion 90 adjacent its second end 74 and the handle member 72 defines an offset portion 91 adjacent its second end 74. The offset portions 90 and 91 define a viewing area 92 which provides a better work area for the user of the tissue approximation forceps 70 when the forceps 70 are moved between the open or uncompressed position shown in FIG. 7 and the closed or compressed position.

The offset portion 90 of the handle member 71 is connected to an outer edge 94 of the grip member 76 while the offset portion 91 of the handle member 72 is connected to an outer edge 95 of the grip member 78. The first and second grip members 76 and 78 extend inwardly from the offset portions 90 and 91.

In the FIG. 7 embodiment, a locking arm 97 extends between the two opposed handle members 71 and 72. In the present embodiment, the locking arm 97 is integrally connected to the handle member 72. The locking arm 97 defines a longitudinally extending rachet 98 along its upper surface. The rachet 98 includes a plurality of teeth 99 defining openings 100 therebetween.

During use, after the wound has been approximated, the handle member 71 is received in one of the aligned openings 100 to secure the second ends 74 of the handle members 71 and 72 and the grip members 76 and 78 in a desired position.

The method of use of the tissue approximation forceps 70 is generally the same as the method discussed above with respect to the method of use of the tissue approximation forceps 10.

Many revisions may be made to the tissue approximation forceps 10, 40 and 70 and to their method of use without departing from the scope of the present invention or from the following claims.

We claim:

1. Tissue approximation forceps for closing a wound or laceration in the skin, said forceps comprising a pair of handle members, said handle members having first ends joined together and second ends, a first grip member mounted to said second end of one of said pair of handle members and a second grip member mounted to said second end of the other one of said pair of handle members, said first and second grip members being positioned to engage the skin on opposite sides of the wound or laceration, said first and second grip members disposed substantially parallel to the surface of the skin adjacent the edges of said wound or laceration, whereby when said second ends of said handle members are moved toward one another said first and second grip members defining a gap after the wound is approximated without everting the skin edges.

2. Tissue approximation forceps, according to claim 1, wherein each of said handle members includes an offset portion adjacent said second ends and adjacent said first and second grip members, said second ends of said handle members being moveable between an uncompressed position and a compressed position, said offset portions of said handle members defining a work area and said grip members defining said gap when said handle members are in such compressed position.

3. Tissue approximation forceps, according to claim 1, wherein said first and second grip members have grip surfaces comprising a plurality of projections that are disposed substantially perpendicular to said surface of the skin adjacent said wound or laceration.

4. Tissue approximation forceps, according to claim 2, wherein said first and second grip members have an outer edge, said offset portion of each of said grip members being connected to said outer edge of said first and second grip members and wherein each of said first and second grip members extend inwardly from said offset portion.

5. Tissue approximation forceps, according to claim 1, wherein each of said handle members includes an inner surface and an outer surface, said handle members defining a textured pattern on said outer surfaces.

6. Tissue approximation forceps, according to claim 1, wherein said tissue approximation forceps are constructed of a metal composition.

7. Tissue approximation forceps, according to claim 1, wherein said tissue approximation forceps are constructed of a plastic material.

8. Tissue approximation forceps, according to claim 7, wherein said plastic material is a polyethylene material.

9. Tissue approximation forceps, according to claim 7, wherein said plastic material is a polybutylene material.

10. Tissue approximation forceps, according to claim 1, wherein each of said first and second grip members are pivotally mounted to said second ends, respectively, of said handle members.

11. Tissue approximation forceps, according to claim 3, wherein said projections comprise a plurality of longitudinally extending, parallel projections, having generally V-shaped cross-sections.

12. Tissue approximation forceps, according to claim 1, including a locking arm extending between said handle members, said locking arm maintaining said second ends of said handle members in a desired position.

13. Tissue approximation forceps, according to claim 12, wherein said locking arm includes a ratchet portion for maintaining said second ends in the desired position.

14. Tissue approximation forceps for closing a wound or laceration in the skin, said forceps comprising a pair handle members having a first ends and a second ends, a first grip member mounted to said second end of one of said pair of handle members and a second grip member mounted to said second end of said other one of said pair of handle members, said first and second grip members being positioned to engage the skin on opposite sides of said wound or laceration, said first and second grip members having a grip surface comprising a plurality of projections that are disposed substantially perpendicular to said surface of said skin adjacent said wound or laceration, said first and second grip members being disposed substantially parallel to the surface of the skin adjacent the edges of said wound or laceration, whereby when said second ends of said handle members are moved toward one another said first and second grip members are in engagement with said skin on opposite sides of said wound or laceration and are moved toward each other to approximate the separated skin tissue, without everting the skin edges.

15. A method for closing a wound or laceration in the skin comprising:

positioning grip members on opposite sides of said wound or laceration, said grip members being disposed to engage said surface of said skin, said grip members remaining substantially parallel to the surface of the skin adjacent the edges of said wound or laceration, and advancing said grip members toward one another to define a gap and approximate the separated skin tissue, without everting the skin edges.

16. A method of approximating a wound or laceration in a patient's skin, comprising the steps of:

moving spaced grip surfaces toward the skin on opposite sides of the wound or laceration;

engaging the skin with said grip surfaces over extended areas with the grip surfaces while remaining generally parallel to the skin surface;

frictionally holding the engaged skin surfaces; and moving said grip surfaces toward one another, to define a gap end approximate the wound or laceration, without everting the skin edges.

17. A method approximating a wound or laceration in a patient's skin, said wound having a longitudinal axis comprising the steps of:

moving spaced grip surfaces carried by joined handle members toward the skin on opposite ends of the wound along such longitudinal axis;

slightly compressing such handle members to generate an outward force while engaging the skin along the longitudinal axis with the grip surfaces remaining generally parallel to the skin surface, frictionally holding the engaged skin surfaces, and using the generated force to move such grip surfaces away from one another to approximate the wound or laceration, without everting the skin edges.

* * * * *

UNITED STATES PATENT AND TRADEMARK OFFICE
CERTIFICATE OF CORRECTION

PATENT NO. : 5,972,021
DATED : October 26, 1999
INVENTOR(S) : James J. Huttner, David I. Kinsel It is certified that error appears in the above-indentified patent and that said Letters Patent is hereby corrected as shown below:

At column 6, in Claim 16, at line 66, "end" should be --and--.

Signed and Sealed this

Third Day of April, 2001

Attest:

NICHOLAS P. GODICI

*Attesting Officer*     *Acting Director of the United States Patent and Trademark Office*